United States Patent
Sato

(10) Patent No.: US 6,788,212 B2
(45) Date of Patent: Sep. 7, 2004

(54) CONDUCTOR DETECTING DEVICE

(75) Inventor: Yoshiharu Sato, Komatsu (JP)

(73) Assignee: Komatsu Ltd., Tokyo (JP)

( * ) Notice: Subject to any disclaimer, the term of this patent is extended or adjusted under 35 U.S.C. 154(b) by 0 days.

(21) Appl. No.: 10/115,014

(22) Filed: Apr. 4, 2002

(65) Prior Publication Data

US 2002/0145530 A1 Oct. 10, 2002

(30) Foreign Application Priority Data

Apr. 6, 2001 (JP) ........................................ 2001-108738

(51) Int. Cl.$^7$ ............................................. G08B 17/10
(52) U.S. Cl. ..................... 340/631; 340/679; 340/682; 340/540; 210/85; 335/306
(58) Field of Search ................. 340/679, 682, 340/540, 649, 664, 660, 631; 335/305, 306; 210/85; 324/71.1, 446

(56) References Cited

U.S. PATENT DOCUMENTS

| | | | |
|---|---|---|---|
| 570,496 A | 11/1896 | Osborn | |
| 2,462,715 A | 2/1949 | Booth | |
| 3,325,009 A | * | 6/1967 | Botstiber et al. ........... 340/679 |
| 3,432,750 A | 3/1969 | Botstiber | |
| 4,008,464 A | * | 2/1977 | Hobbie ....................... 335/305 |
| 4,323,843 A | 4/1982 | Batham | |
| 4,564,448 A | * | 1/1986 | O'Meara, Jr. ............... 210/222 |
| 5,027,065 A | * | 6/1991 | Bares et al. ................ 340/631 |
| 5,179,346 A | 1/1993 | McGee et al. | |

FOREIGN PATENT DOCUMENTS

| | | |
|---|---|---|
| JP | 613466 | 2/1986 |
| JP | 05142175 | 6/1993 |
| JP | 06082562 | 3/1994 |
| JP | 09304353 | 11/1997 |

* cited by examiner

Primary Examiner—Anh V. La
(74) Attorney, Agent, or Firm—Varndell & Varndell, PLLC

(57) ABSTRACT

A device capable of reducing an erroneous operation with a simple configuration in which, when two or more conductors M1, M2, M3 (three of them in FIG. 1) are attracted by three or more magnets 1a, 1b, 1c, 1d (four of them in FIG. 1), the conductors M1, M2, M3 are electrically connected between the respective magnets to bring a series circuit 3 into conduction that causes an electric current Is to flow, whereby an electric signal (voltage) Vs(=V) indicating the detection of the conductors M1, M2, M3 is output.

10 Claims, 4 Drawing Sheets

CONDUCTOR DETECTING DEVICE

BACKGROUND OF THE INVENTION

1. Field of the Invention

The present invention relates to a conductor detecting device. More specifically, the invention relates to a conductor detecting device which has a simple structure and can reduce erroneous operations.

2. Description of the Related Art

A gearbox accommodating gears is filled with a lubricating oil. When the gears are driven, the gears in mesh produce fine particles or fragments as metal powder or metal shards, which are mingled in the lubricating oil.

A bearing box which accommodates a bearing is also filled with the lubricating oil. When a shaft is driven, fine particles or fragments are produced as metal powder or metal shards from the sliding surfaces of the bearing and the shaft and are mingled in the lubricating oil.

The fine particles or fragments of the gears may be caught by the normal gears or clog a lubricating oil passage in the bear box, causing an adverse effect. And, when the abrasion or damage of the bearing proceeds, the drive of the shaft is adversely affected.

Therefore, detection of the metal powder or metal shards mingled in the lubricating oil enables to judge whether a level of abrasion or damage of the gears or bearing has exceeded a prescribed level.

The gears and bearing are made of metal and are conductors. Accordingly, the gearbox or the bearing box is provided with a metal detecting device for detecting a conductor such as metal powder, metal shards or the like produced due to abrasion or chipping out of the gears or bearing.

FIG. 7 is a diagram showing a structure of a conventional metal detecting device 72 which is disposed in a gearbox.

The metal detecting device 72 is provided with a detecting section 71. The detecting section 71 is provided with two magnets 70a, 70b, which attract metal powder or metal shard M and are disposed with a space between them so to be electrically insulated. In the detection section 71, electric current Ix, which indicates the detection of the metal powder or metal shard M, flows through a circuit when the magnets are electrically connected by the metal powder or metal shard M which is attracted by the two magnets 70a, 70b. The current Ix is directly converted into a warning signal and output or processed as accumulated data, output warning signal or the like by an unshown controller. When the warning signal is output, it can be judged that the abrasion or damage of the gears has exceeded a prescribed level.

When machining to produce the gears, swarf is produced. The swarf often stays on the gear surface even if the gear surface is washed. The swarf adhered to the gear surface is mingled into the lubricating oil.

Furthermore, when the gearbox is being machined, cuttings are produced as metal powder or metal shards. Such cuttings might remain adhered to the inside surface of the gearbox even if the gearbox interior is washed. Therefore, the cuttings adhered to the inside surface of the gearbox are also mingled into the lubricating oil.

There is also a possibility that when the gears are being checked for maintenance, a metal foreign material, which is different from the fine particles or fragments of the gears, is externally mingled into the lubricating oil in the gearbox.

Here, the fine particles or fragments of the gears are attracted by the magnets 70a, 70b so to electrically connect the magnets, so that the current Ix flows, and the warning signal is output.

But, the metal detecting device 72 is provided with only one detecting section 71, so that the current Ix flows and the warning signal is output when the swarf, cuttings or metal foreign material is attracted to the magnets 70a, 70b to electrically connect the magnets.

Thus, the metal detecting device 72 had an erroneous operation that a warning signal was output because the current Ix flows when swarf, cuttings or metal foreign material, which is mingled in the same manner as the fine particles or fragments of the gears, is attracted by the magnets 70a, 70b to electrically connect the magnets.

For example, Japanese Utility Model Laid-Open Publication No. SHO61-3466 discloses a metal detecting device which is provided with a plurality of detecting sections.

FIG. 8 is a diagram showing the metal detecting device described in Japanese Utility Model Laid-Open Publication No. SHO61-3466.

Metal detecting device 83 of FIG. 8 is configured to have a parallel circuit 82 by disposing a plurality of detecting sections (magnet devices) 81, each of which has two magnets 80a, 80b disposed with a space between them to attract metal (magnetic foreign material). According to this metal detecting device 83, when metal is attracted to any one of the plural detecting sections 81, 81, . . . , the parallel circuit 82 is brought into conduction, and a current indicating the detection of metal flows through the circuit.

The metal detecting device 83 of FIG. 8 is configured to improve its reliability of metal detection by disposing the plural detecting sections 81. Therefore, according to this conventional metal detecting device 83, the swarf, cuttings or metal foreign material, which is mingled in the same manner as the fine particles or fragments of the gears, is detected without fail. Thus, the problem of causing an erroneous operation remains unsolved.

For example, the conventional metal detecting device 83 can remedy an erroneous operation by incorporating a logical circuit or performing a judging process by inputting output signals of the plural detecting sections 81, 81, . . . , to the controller and, when metal is detected by any one of the plural detecting sections 81, 81, . . . , judging that metal is not detected, and when metal is detected by two or more detecting sections 81, 81, . . . , judging that metal is detected.

But, addition of the controller to a conventional metal sensor has a disadvantage that the structure become complex and the cost becomes high.

SUMMARY OF THE INVENTION

The present invention has been achieved under the above circumstances, and it is an object of the invention to reduce an erroneous operation by a simple structure.

To achieve the above object, a first aspect of the invention is directed to a conductor detecting device which detects conductors by attracting the conductors to a plurality of magnets, wherein three or more magnets are disposed with spaces between the respective magnets to configure a series circuit; and the conductors are attracted by the three or more magnets so to be electrically connected between the respective magnets to bring the series circuit into conduction, and an electric signal indicating the detection of the conductors is output.

The first aspect of the invention will be described with reference to FIG. 1.

According to the first aspect of the invention, when two or more conductors M1, M2, M3 (three conductors in FIG. 1) are attracted to three or more magnets 1a, 1b, 1c, 1d (four magnets in FIG. 1), the conductors M1, M2, M3 are electrically connected between the respective magnets, and a series circuit 3 is brought into conduction to cause a current Is to flow. Thus, an electric signal (voltage Vs (=V) indicating the detection of the conductors M1, M2, M3 is output.

According to the first aspect of the invention, when two or more conductors are attracted between the three or ore magnets, the series circuit 3 is brought into conduction for the first time to output the electric signal Vs (=V). Therefore, when only one of the mingled swarf, cuttings or metal foreign material is attracted between the magnets, the electric signal Vs (=V) is not output, and when two or more metals are attracted between three or more magnets, the electric signal Is is output, so that an erroneous operation due to the attraction of one foreign material or the line is not caused.

By disposing the three or more magnets 1a, 1b, 1c, 1d with a space between them to configure the series circuit 3, an erroneous operation can be prevented, and addition of a controller to a metal sensor is not needed unlike a conventional art, so that the structure can be made simple, and the cost can be reduced.

A second aspect of the invention relates to the first aspect of the invention, wherein the three or more magnets are arranged around the outer periphery of a rod member.

The second aspect of the invention will be described with reference to FIG. 2.

According to the second aspect of the invention, the three or more magnets 1a, 1b, 1c, 1d are arranged around the outer periphery of the rod member 20.

A third aspect of the invention relates to the first aspect of the invention, wherein the three or more magnets are arranged concentrically.

The third aspect of the invention will be described with reference to FIGS. 4(a), (b).

According to the third aspect of the invention, three or more magnets 40a, 40b, 40c are arranged concentrically.

A fourth aspect of the invention relates to the first aspect of the invention, wherein the three or more magnets are arranged in a circumferential direction.

The fourth aspect of the invention will be described with reference to FIG. 5.

According to the fourth aspect of the invention, three or more magnets 50a, 50b, 50d, 50d are arranged in a circumferential direction.

A fifth aspect of the invention relates to the first aspect of the invention, wherein the three or more magnets are arranged in parallel.

The fifth aspect of the invention will be described with reference to FIG. 6.

According to the fifth aspect of the invention, three or more magnets 60a, 60b, 60c are arranged in parallel.

DESCRIPTION OF THE PREFERRED EMBODIMENTS

Now, embodiments of the conductor detecting device to which the present invention pertains will be described with reference to the accompanying drawings. It is assumed in the following embodiments that the conductor detecting device is a metal detecting device which detects metal mingled in a lubricating oil due to abrasion of metallic gears.

Figure 1:
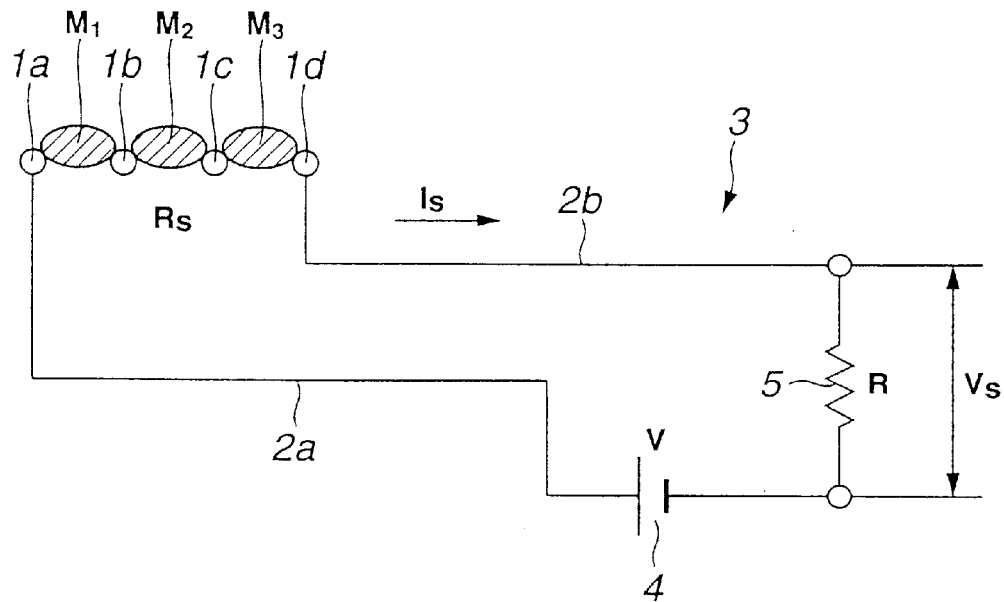
FIG. 1 is an electric circuit diagram showing an embodiment of the present invention.

FIG. 1 is an electric circuit diagram showing the metal detecting device of this embodiment.

As shown in FIG. 1, the metal detecting device is broadly comprised of four magnets 1a, 1b, 1c, 1d, a power supply 4, an output resistor 5, electric signal wires 2a, 2b and a series circuit 3.

The series circuit 3 is configured of the four magnets 1a, 1b, 1c, 1d, the power supply 4 and the output resistor 5 which are connected in series.

The magnets 1a, 1b, 1c, 1d are separately arranged to detect conductor metals M1, M2, M3. In this embodiment, it is assumed that M1 is not fine particles or fragments of the gears but swarf (or cuttings, metal foreign materials), and M2, M3 are fine particles or fragments of the gears.

It is assumed that a gap between the magnets 1a and 1b, a gap between the magnets 1b and 1c and a gap between the magnets 1c and 1d are respectively set to such a level that a worn or damaged level of gears has exceeded a prescribed threshold value.

The positive terminal of the power supply 4 is connected to the magnet 1c through the electric signal wire 2a. And, the negative terminal of the power supply 4 is connected to the magnet 1d through the electric signal wire 2b and the output resistor 5.

The series circuit 3 is configured by disposing the four magnets 1a, 1b, 1c, 1d with a space among them as described above. It is assumed that a voltage of the power supply 4 is V, a resistance among all the magnets (which is called as a detection section resistance) is Rs, the output resistor is R, and voltages of both ends of the output resistor 5 (called as monitoring voltage) are Vs.

When the magnets 1a and 1b, the magnets 1b and 1c and the magnets 1c and 1d are electrically connected by the metals M1, M2 and M3, the series circuit 3 is brought into conduction, and electric current Is which indicates the detection of the metals M1, M2, M3 passes through the series circuit 3. Thus, the monitoring voltage Vs at either end of the output resistor 5 becomes the voltage Vs (=V) corresponding to the electric current Is as described later. When the monitoring voltage Vs becomes the voltage Vs (=V) corresponding to the current Is, a warning signal is output to the outside.

Figure 2:
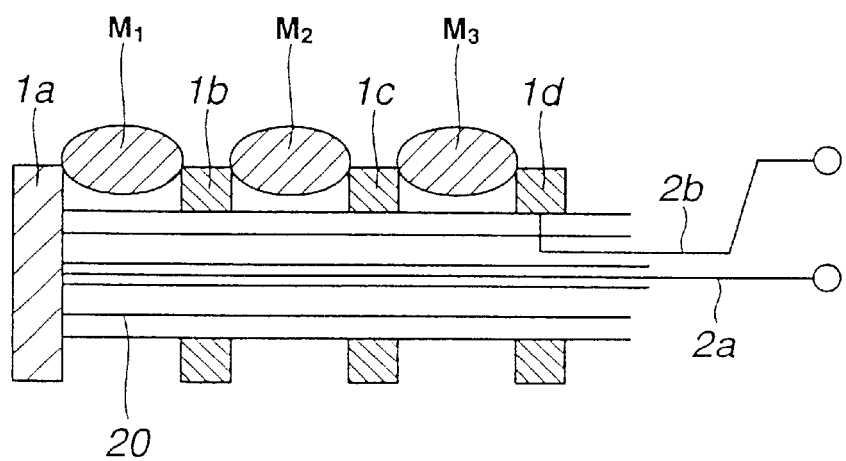
FIG. 2 is a diagram showing a first layout example of magnets of FIG. 1.

FIG. 2 shows a layout example of the magnets 1a, 1b, 1c, 1d.

As shown in FIG. 2, the magnets 1a, 1b, 1c, 1d are arranged around the outer periphery of a cylindrical rod member 20. The magnets 1a, 1b, 1c, 1d are arranged in a longitudinal direction of the rod member 20. The electric signal wires 2a, 2b are disposed in a hollow section of the rod member 20.

Figure 3:
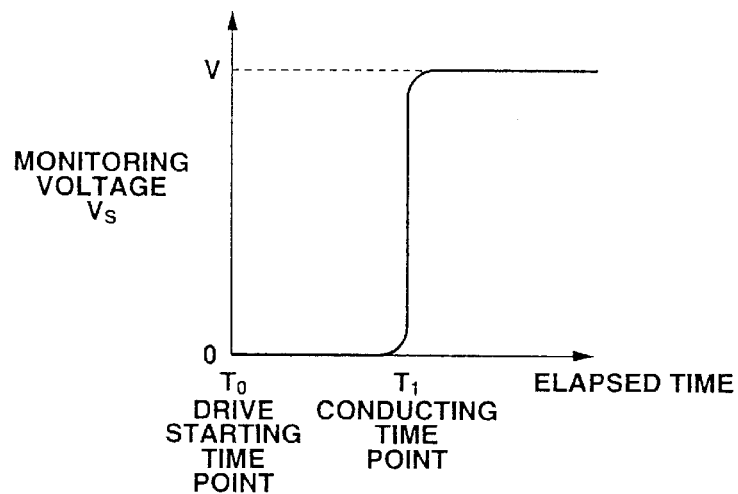
FIG. 3 is a diagram showing a state that a monitoring voltage varies according to a duration elapsed after driving equipment.

Then, an operation of the metal detecting device shown in FIG. 1 will be described with reference to FIG. 1, FIG. 2 and FIG. 3. FIG. 3 is a diagram showing a state that the monitoring voltage Vs is varied according to a time elapsed after the gears are driven.

It is assumed that swarf M1 is suddenly mixed into the lubricating oil at an initial stage when the gears are started to drive. The swarf M1 is attracted to the magnets 1a, 1b within a period of time T0 to time T1, and the magnets 1a, 1b are electrically connected by the swarf M1. But, the magnets 1b and 1c and the magnets 1c and 1d are not electrically connected. Therefore, the series circuit 3 is not brought into conduction, and the electric current Is does not flow. The monitoring voltage Vs at this time will be described.

When electrical connection is not established between the magnets 1b and 1c and between the magnets 1c and 1d, the detecting section resistance Rs is as follows:

$$Rs = \infty \quad (1)$$

The monitoring voltage Vs is determined as follows:

$$Vs = (R/R+Rs) \cdot V \quad (2)$$

Therefore, from the above expressions (1) and (2), the monitoring voltage Vs when no electrical connection is established between the magnets 1b and 1c and between the magnets 1c and 1d is determined as follows:

$$Vs \approx 0 \quad (3)$$

When the monitoring voltage Vs is 0, a warning signal is not output to the outside. Specifically, when the swarf M1 is mingled in the lubricating oil within a period of from drive starting time point T0 to conducting time point T1, error detection resulting in the output of a warning signal can be prevented.

Then, it is assumed that the gears are gradually worn and fine particles M2, M3 are produced and mingled into the lubricating oil. The fine particles M2, M3 are attracted between the magnets 1b and 1c and between the magnets 1c and 1d at time T1, and the electrical connection is established between the magnets 1b and 1c and between the magnets 1c and 1d by the fine particles M2, M3. And, the magnets 1a and 1b have been electrically connected by the swarf M1.

Thus, when the electrical connection is established between the magnets 1a and 1b, between the magnets 1b and 1c and between the magnets 1c and 1d, the series circuit 3 is brought into conduction, and the electric current Is flows it. The monitoring voltage Vs at the time will be considered.

When the electrical connection is established between the magnets 1a and 1b, between the magnets 1b and 1c and between the magnets 1c and 1d, the detecting section resistance Rs is determined as follows:

$$Rs \approx 0 \quad (4)$$

The monitoring voltage Vs is determined from the above expression (2) (Vs=(R/R+Rs)·V).

Thus, from the above expression (2) and (4), when the electrical connection is established between the magnets 1a and 1b, between the magnets 1b and 1c and between the magnets 1c and 1d, the monitoring voltage Vs is determined as follows:

$$Vs \approx V \quad (5)$$

When the monitoring voltage Vs is V, a warning signal is output to the outside. Namely, when the gears are worn and their worn level exceeds a prescribed limit, the warning signal is output.

Similarly, when a gear is chipped and the fragments M2, M3 are attracted between the magnets 1b and 1c and between the magnets 1c and 1d, the warning signal is also output.

According to this embodiment described above, the series circuit 3 is brought into conduction for the first time when the three metals M1, M2, M3 are attracted between the magnets (between the magnets 1a and 1b, 1b and 1c, and 1c and 1d), the monitoring voltage Vs becomes the power voltage V, and the warning signal is output. Therefore, the attraction of only one of the mingled swarf, cuttings and metal foreign material M1 between the magnets 1a and 1b does not output a warning signal. The warning signal is output only when the two metals M2, M3 are attracted between the magnets 1b and 1c and between the magnets 1c and 1d. Thus, an erroneous operation due to the attraction of a single foreign material or the like can be prevented.

According to this embodiment, an erroneous operation can be prevented by the series circuit 3 configured by disposing the four magnets 1a, 1b, 1c and 1d with spaces therebetween. And, a controller is not required to be added to a metal sensor unlike a conventional art, so that the structure can be simplified, and the cost can be reduced.

In this embodiment, it is assumed that the four magnets 1a, 1b, 1c, 1d are disposed to attract the three magnets M1, M2, M3.

But, the present invention can dispose at least three magnets to attract at least two metals M1, M2.

For example, when three magnets 1a, 1b, 1c are disposed and two metals M1, M2 are attracted between two magnets (between the magnets 1a and 1b and between the magnets 1b and 1c), the series circuit 3 is brought into conduction for the first time, the monitoring voltage Vs becomes the power voltage V, and the warning signal is output. Attraction of at least one of the mingled swarf, cuttings and metal foreign material M1 between the magnets 1a and 1b does not output the warning signal. And, only when the other metal M2 is attracted between the magnets 1b and 1c, the warning signal is output, so that an erroneous operation due to the attraction of a single foreign material or the like can be prevented.

As shown in FIG. 2, the magnets 1a, 1b, 1c, 1d are arranged around the outer periphery of the cylindrical rod member 20 but they may be arranged in any form. For example, magnets 40a, 40b, 40c may be arranged concentrically as shown in FIGS. 4(a) and 4(b).

Figure 4A:
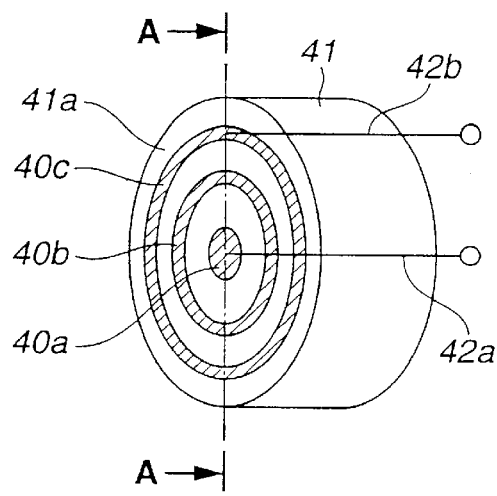
FIGS. 4(a) and 4(b) are diagrams showing a second layout example of the magnets of FIG. 1.
Figure 4B:
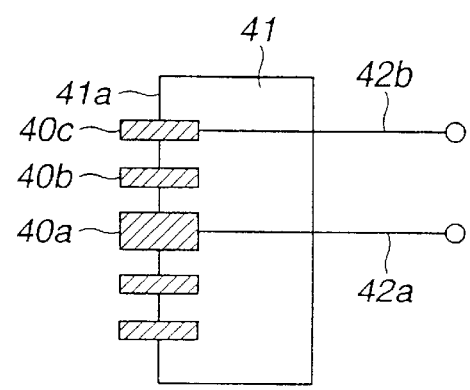

FIG. 4(a) is a perspective diagram showing an appearance of a sensor which has the magnets 40a, 40b, 40c arranged concentrically, and FIG. 4(b) is a sectional diagram taken along line A—A of FIG. 4(a).

As shown in FIG. 4(a), the magnets 40a, 40b, 40c are concentrically arranged on a flat surface 41a of a disc member 41. The flat surface 41a of the disc member 40 is immersed in a lubricating oil. An electric signal wire 42a is connected to the magnet 40 at the center of the concentric circles and an electric signal wire 42b is connected to the magnet 40c at the outermost position of the concentric circles. The magnets 40a, 40b, 40c correspond to the magnets 1a, 1b, 1c, 1d of FIG. 1, and the electric signal wires 42a, 42b correspond to the electric signal wires 2a, 2b of FIG. 1. Therefore, when the metals M1, M2 are attracted between the magnets 40a and 40b and between the magnets 40b and 40c respectively, electric current Is flows through the electric signal wires 42a, 42b, the monitoring voltage Vs becomes the power voltage V, and the warning signal is output to the outside.

Figure 5:
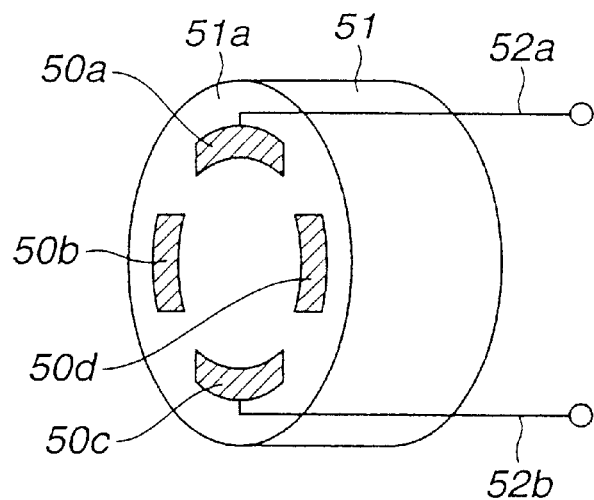
FIG. 5 is a diagram showing a third layout example of the magnets of FIG. 1.

Magnets 50a, 50b, 50c 50d may be arranged in a circumferential direction as shown in FIG. 5.

The magnets 50a, 50b, 50c, 50d are arranged in the circumferential direction on a flat surface 51a of a disc member 51 as shown in FIG. 5. The flat surface 51a of the disc member 51 is immersed in a lubricating oil. An electric signal wire 52a is connected to the magnet 50a, and an electric signal wire 52b is connected to the magnet 50c.

The magnets 50a, 50b, 50c, 50d correspond to the magnets 1a, 1b, 1c, 1d of FIG. 1, and electric signal wires 52a, 52b correspond to the electric signal wires 2a, 2b of FIG. 1. Therefore, when the metals M1, M2 are attracted between the magnets 50a and 50b and between the magnets 50b and 50c, the electric current Is flows through the electric signal wires 52a, 52b, the monitoring voltage Vs become the power voltage V, and the warning signal is output to the outside. And, when metals M1, M2 are attracted between the magnets 50a and 50d and between the magnets 50d and 50c respectively, the electric current Is flows through the electric signal wires 52a, 52b, the monitoring voltage Vs becomes the power voltage V, and the warning signal is output to the outside.

Figure 6:
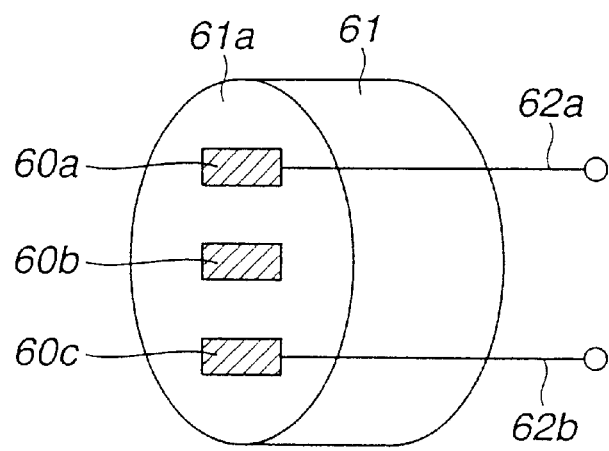
FIG. 6 is a diagram showing a fourth layout example of the magnets of FIG. 1.
Figure 7:
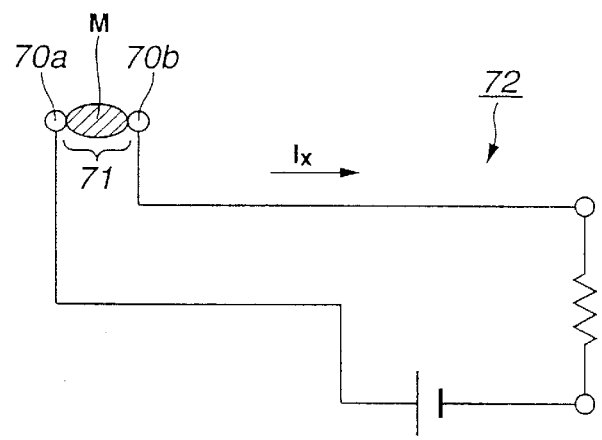
FIG. 7 is a diagram showing a conventional art.
Figure 8:
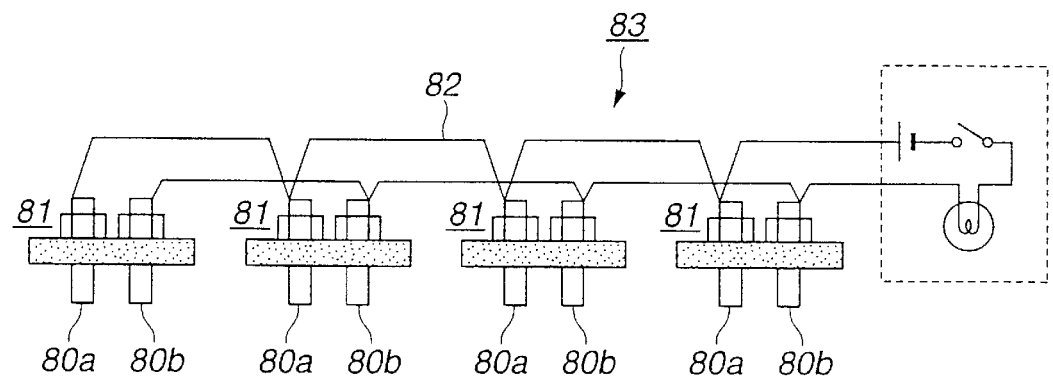
FIG. 8 is a diagram showing a conventional art different from FIG. 7.

As shown in FIG. 6, magnets 60a, 60b, 60c may be arranged in parallel.

The magnets 60a, 60b, 60c are arranged in parallel on a flat surface 61a of a disc member 61 as shown in FIG. 6. The flat surface 61a of the disc member 61 is immersed in a lubricating oil. An electric signal wire 62a is connected to the magnet 60a, and an electric signal wire 62b is connected to the magnet 60c.

The magnets 60a, 60b, 60c correspond to the magnets 1a, 1b, 1c, 1d of FIG. 1, and the electric signal wires 62a, 62b correspond to the electric signal wires 2a, 2b of FIG. 1. Therefore, when the metals M1 and M2 are attracted between the magnets 60a and 60b and between the magnets 60b and 60c, the current Is flows through the electric signal wires 62a, 62b, the monitoring voltage Vs becomes the power voltage V, and the warning signal is output to the outside.

In the embodiment described above, it was assumed that abrasion of the metallic gears was detected, but the invention can also be applied to a case of detecting the abrasion of metallic bearings.

In this embodiment, it was assumed that metal in a lubricating oil was detected, but the invention can also be applied to the detection of metal in a hydraulic oil of a hydraulic machine. Furthermore, the invention may be applied to the detection of metal mingled into a coolant for cooling an engine other than the detection in oil. And, the invention can also be applied to the detection of a general conductor other than metal.

What is claimed is:

1. A conductor detecting device which detects conductors by attracting the conductors to a plurality of magnets, wherein:

three or more magnets are disposed with spaces between the respective magnets; and one of the three or more magnets is connected to a negative terminal of a power source and another one of the three or more magnets is connected to a positive terminal of the power source, whereby a plurality of spaces defined between each of the three or more magnets are made part of a series circuit; and the series circuit is brought into electrical conduction when the conductors are attracted to all of the spaces between each of the three or more magnets and outputs a warning signal.

2. The conductor detecting device according to claim 1, wherein the three or more magnets are arranged around an outer periphery of a rod member.

3. The conductor detecting device according to claim 1, wherein the three or more magnets are arranged concentrically.

4. The conductor detecting device according to claim 1, wherein the three or more magnets are arranged along a circumferential direction.

5. The conductor detecting device according to claim 1, wherein the three or more magnets are arranged in parallel.

6. A conductor detecting device for detecting conductors by attracting the conductors to a plurality of magnets, which comprises:

a series circuit including three or more magnets arranged with nonconductive spaces between the respective magnets;

the conductors being attracted to the three or more magnets and filling all the nonconductive spaces between the respective magnets for electrically connected the three or more magnets together to complete the series circuit, and the series circuit outputting an electric signal when the series circuit is completed.

7. The conductor detecting device according to claim 6, wherein the three or more magnets are arranged around an outer periphery of a rod member.

8. The conductor detecting device according to claim 6, wherein the three or more magnets are arranged concentrically.

9. The conductor detecting device according to claim 6, wherein the three or more magnets are arranged along a circumferential direction.

10. The conductor detecting device according to claim 6, wherein the three or more magnets are arranged in parallel.

* * * * *